US006932602B2

United States Patent
Hamilton et al.

(10) Patent No.: US 6,932,602 B2
(45) Date of Patent: Aug. 23, 2005

(54) DENTAL ARTICULATION KIT AND METHOD

(75) Inventors: Timothy Hamilton, Griffin, GA (US); Ted E. Goodwin, Appleton, WI (US)

(73) Assignee: Appleton Papers Inc., Appleton, WI (US)

( * ) Notice: Subject to any disclaimer, the term of this patent is extended or adjusted under 35 U.S.C. 154(b) by 301 days.

(21) Appl. No.: 10/420,663

(22) Filed: Apr. 22, 2003

(65) Prior Publication Data

US 2004/0214134 A1 Oct. 28, 2004

(51) Int. Cl.[7] .................................. A61C 9/00
(52) U.S. Cl. .......................... 433/70; 433/71
(58) Field of Search ............. 433/70, 71; 428/488.11, 428/488.41

(56) References Cited

U.S. PATENT DOCUMENTS

| | | |
|---|---|---|
| RE23,024 E | 8/1948 | Adams |
| 2,730,456 A | 1/1956 | Green et al. |
| 2,800,457 A | 7/1957 | Green et al. |
| 3,041,289 A | 6/1962 | Katchen et al. |
| 3,244,550 A | 4/1966 | Farnham et al. |
| 3,421,223 A | 1/1969 | Stark |
| 3,455,721 A | 7/1969 | Phillips, Jr. et al. |
| 3,491,111 A | 1/1970 | Lin |
| 3,491,112 A | 1/1970 | Lin |
| 3,491,116 A | 1/1970 | Lin |
| 3,509,174 A | 4/1970 | Lin |
| 3,565,666 A | 2/1971 | Phillips, Jr. |
| 3,622,364 A | 11/1971 | Sugahara et al. |
| 3,624,107 A | 11/1971 | Lin |
| 3,627,581 A | 12/1971 | Phillips, Jr. |
| 3,627,787 A | 12/1971 | Lin |
| 3,641,011 A | 2/1972 | Lin et al. |
| 3,642,828 A | 2/1972 | Farber et al. |
| 3,672,935 A | 6/1972 | Miller et al. |
| 3,681,390 A | 8/1972 | Lin |
| 3,732,120 A | 5/1973 | Brockett et al. |
| 3,737,410 A | 6/1973 | Mueller |
| 3,753,761 A | 8/1973 | Sugahara et al. |
| 3,775,424 A | 11/1973 | Farber |
| 3,806,463 A | 4/1974 | Konishi et al. |
| 3,853,869 A | 12/1974 | Farber |
| 3,920,510 A | 11/1975 | Hatano et al. |
| 3,955,026 A | 5/1976 | Matsukawa et al. |
| 3,959,571 A | 5/1976 | Yahagi et al. |
| 3,959,881 A | 6/1976 | Kokal, Jr. |
| 3,971,808 A | 7/1976 | Baumann et al. |
| 3,996,405 A | 12/1976 | Porter, Jr. |
| 4,001,140 A | 1/1977 | Foris et al. |
| 4,022,936 A | 5/1977 | Miller et al. |
| 4,027,065 A | 5/1977 | Brockett et al. |
| 4,081,376 A | 3/1978 | Strub |
| 4,089,802 A | 5/1978 | Foris et al. |
| 4,100,103 A | 7/1978 | Foris et al. |

(Continued)

Primary Examiner—Cary E. O'Connor
Assistant Examiner—Candice C. Stokes
(74) Attorney, Agent, or Firm—Banner & Witcoff, Ltd.

(57) ABSTRACT

A method for performing a dental articulation test and a related test kit are provided. In preferred embodiments, the method includes applying a first chemical component of a binary marking system to at least one tooth of a patient or articulation device. A substrate sheet that contains a coating of microcapsules disposed on at least one side thereof, with at least some of the microcapsules containing a second chemical component of the binary marking system is inserted into the patient's mouth or the articulation device. The first and second arches of the patient or articulation device are then caused to occlude over the substrate, thereby causing formation of a visible mark at the occlusion contact points. The dental articulation kit includes the substrate sheet, an applicator for applying the first chemical component of the binary marking system to teeth, and a quantity of the first chemical component of the binary marking system sufficient to apply to at least one tooth.

66 Claims, 3 Drawing Sheets

U.S. PATENT DOCUMENTS

| | | |
|---|---|---|
| 4,105,823 A | 8/1978 | Hasler et al. |
| 4,130,299 A | 12/1978 | Wygant |
| 4,165,102 A | 8/1979 | Bodmer |
| 4,165,103 A | 8/1979 | Bodmer |
| 4,166,644 A | 9/1979 | Kay et al. |
| 4,188,456 A | 2/1980 | Patel |
| 4,246,318 A | 1/1981 | Baum |
| 4,287,074 A | 9/1981 | Earhart et al. |
| 4,444,699 A | 4/1984 | Hayford |
| 4,510,513 A | 4/1985 | Yamaguchi et al. |
| 4,522,811 A | 6/1985 | Eppstein et al. |
| 4,596,998 A | 6/1986 | Krimmel |
| 5,141,915 A * | 8/1992 | Roenigk et al. ............ 503/227 |
| 5,177,051 A | 1/1993 | Hobson et al. |
| 5,281,266 A | 1/1994 | Sheiham et al. |
| 5,458,487 A | 10/1995 | Komatsu et al. |
| 5,464,803 A | 11/1995 | McGuinness et al. |
| 5,472,489 A | 12/1995 | Sheiham et al. |
| 5,474,967 A | 12/1995 | Komatsu et al. |
| 5,476,829 A | 12/1995 | Taylor et al. |
| 5,605,874 A | 2/1997 | Taylor et al. |
| 6,152,731 A | 11/2000 | Jordan et al. |
| 6,310,002 B1 | 10/2001 | Krzoska et al. |
| 6,322,359 B1 | 11/2001 | Jordan et al. |
| 6,334,853 B1 | 1/2002 | Kopelman et al. |
| 2003/0175653 A1 * | 9/2003 | Tesini ..................... 433/71 |

* cited by examiner

DENTAL ARTICULATION KIT AND METHOD

FIELD OF THE INVENTION

This invention pertains to dental articulation kits as well as methods for performing dental articulation.

BACKGROUND OF THE INVENTION

Dental articulation is a methodology used to determine the occlusion contact points between upper and lower teeth. Articulation is useful in a variety of dental treatments and can be used for instance, in determining the size, shape and proper placement of bridges, caps, crowns and fillings and in observing the progress of an orthodontic treatment program. Articulation methods can be performed on the actual teeth of a patient or on a dental articulation device which, for example, consists of a model of all or a portion of a patient's oral cavity that replicates movement of the patient's jaws. These articulation devices are frequently used to help design replacements for the missing or damaged teeth of a patient and to test the fit of orthodontic appliances such as braces.

Dental articulation tests are commonly performed by inserting carbon paper between the upper and lower dental arches of the patient. The patient then bites strongly on the carbon paper to occlude the upper and lower teeth. Carbon particles adhere on the occlusal surfaces of the teeth where the upper and lower teeth are abutted. The dental practioner can then diagnose the occlusion condition of the teeth by observing the positions and areas of the portions to which carbon particles stick.

Unfortunately, articulation tests performed using carbon paper frequently produce results that do not accurately reflect the precise occlusion contact points. For example, carbon paper articulation tests often produce false spots or false lines. Additional problems with carbon paper that detract from the accuracy of articulation tests include clumping and smudging of the carbon. These problems can be exacerbated by the saliva present in the patient's mouth.

Another problem with dental articulation tests performed using carbon paper is that the carbon does not always transfer well to a patient's teeth. As a result, a patient sometimes must bite down on the carbon paper several times in order to get good transfer of the carbon to the teeth. Often, the patient may have to grind the carbon paper between his teeth to ensure good carbon transfer.

BRIEF SUMMARY OF THE INVENTION

The invention provides a dental articulation kit and method which overcomes the problems with conventional carbon paper articulation tests as well as offers other features and advantages. In particular, according to one embodiment of the present invention, a method for dental articulation is provided which includes applying an absorbent material that includes a first chemical component of a binary marking system to a tooth of a patient. At least a portion of the first chemical component is allowed to deposit on to the tooth and at least a portion of the patient's saliva is allowed to become absorbed by said absorbent material. A substrate that includes a second chemical component of the binary marking system is inserted into the patient's mouth. The patient's teeth are then caused to occlude over the substrate thereby causing formation of a visible mark at occlusion contact points.

According to another embodiment of the present invention, a dental articulation kit is provided that includes an absorbent substrate including an absorbent material and a first chemical component of a binary marking system. The kit further includes a second substrate including a second chemical component of the binary marking system. The first and second substrates are sized for human dental articulation and the absorbent substrate is relatively more absorbent than said second substrate.

In yet another embodiment of the present invention, a method for dental articulation is provided that includes applying a first chemical component of a binary marking system to at least one tooth of a patient or articulation device. A substrate sheet that contains a coating of microcapsules disposed on at least one side thereof, with at least some of the microcapsules containing a second chemical component of the binary marking system, is inserted into the patient's mouth or the articulation device. The first and second arches of the patient or articulation device are then caused to occlude over the substrate, thereby causing formation of a visible mark at occlusion contact points.

According to a further embodiment of the present invention, a dental articulation kit is provided that includes at least one substrate having first and second sides and including a coating of a microencapsulated first binary chemical component of a binary marking system disposed on at least one of the first and second sides. The kit also includes a quantity of a second binary chemical component of the binary marking system sufficient to apply to at least one tooth of a patient or articulation device to enable dental articulation and an applicator for applying the second binary chemical component to at least one tooth of a patient or articulation device.

In another embodiment of the present invention, a method for dental articulation is provided that includes the step of applying a substrate sheet that includes a coating of microcapsules disposed on at least one side thereof to at least one tooth of a patient or articulation device. The first and second arches of the patient or articulation device are then caused to occlude over the substrate whereby at least some of the microcapsules rupture thereby releasing a material contained in the microcapsules at occlusion contact points. The release of material from the microcapsules causes light to be emitted from the tooth at the occlusion contact points.

In another embodiment, the invention provides a method in which a mixture of first and second components of a binary marking system is applied to a tooth of a patient or articulation device. The first and second components are separate in the mixture but are reactive to form a visible mark upon the application of pressure. The teeth of the patient or device are caused to occlude, thereby forming a visible mark at occlusion contact points. A kit that includes such mixture and an applicator also falls within the purview of the invention.

In another embodiment, the first and second components of a binary marking system are applied separately to first and second contacting teeth of a patient or articulation device. In this embodiment, the first and second components are reactive to form a visible mark upon the application of pressure. The teeth of the patient or device are caused to occlude, thereby forming a visible mark at occlusion contact points. A kit that includes the first and second components and an applicator also is encompassed by the invention.

The invention further contemplates a method for dental articulation in which a light-emitting material is applied to the tooth of a patient or articulation device. First and second arches of the patient or device are caused to occlude, thereby leaving a mark at occlusion contact points. A device that comprise a substrate on which is disposed a light-emitting material that is transferable to a tooth upon the application of pressure also is encompassed by the invention. The device is useful in the practice of the foregoing method.

DETAILED DESCRIPTION OF THE PREFERRED EMBODIMENTS

Figure 1:
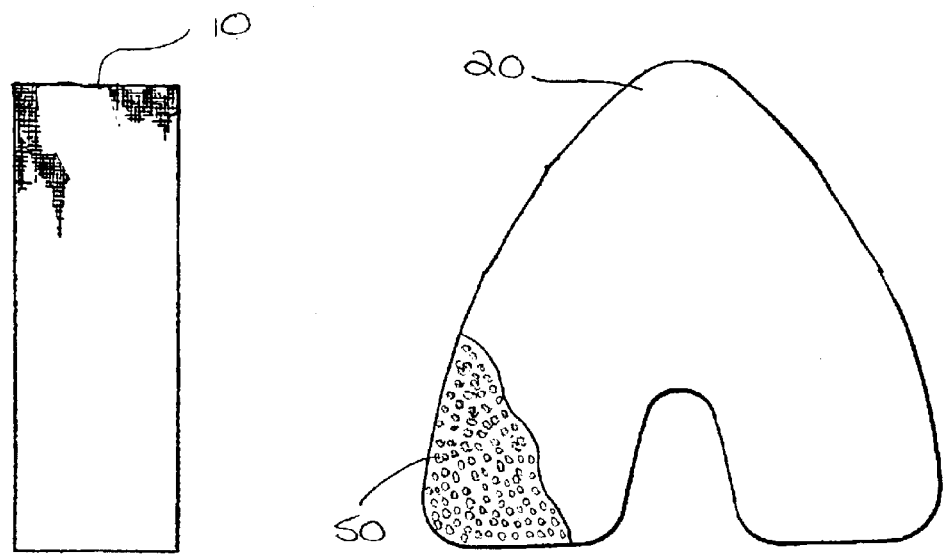
FIG. 1 is a plan view of an exemplary dental articulation kit according to the present invention.

Referring now to FIG. 1 of the drawings, the illustrated kit utilizes a binary marking system consisting of first and second chemical components that produce a visible effect such as color formation when they are intermixed. It is contemplated that the "color" may be a black, gray, or other visible indicia, such as a light-emitting indicia. The illustrated kit includes an applicator substrate 10 and an occlusion substrate 20. In general, the two substrates 10, 20 are usable to situate the two components of the binary marking system in the mouth of a patient, or with respect to a dental articulation device, such that when the upper and lower teeth 30, 40 of the patient or dental articulation device occlude, the two chemicals intermix causing formation of a visible mark at the occlusion contact points on the teeth.

To this end, the applicator substrate 10 in the illustrated kit is useable to apply a first chemical component of the binary marking system to the teeth of the patient or articulation device on which the articulation test is to be performed. The kit can further include a quantity of the first chemical component of the binary marking system sufficient to apply to at least one tooth. In practice, the first chemical component generally will be applied to a plurality of teeth in both upper and lower dental arches, however, the present invention can be practiced in connection with only a single tooth. The occlusion substrate 20 includes the second chemical component of the binary marking system. The occlusion substrate 20 is insertable into the patient's mouth or the articulation device between the upper and lower teeth 30,40 (see FIG. 2). When the upper and lower teeth 30, 40 of the patient or articulation device occlude over the occlusion substrate 20, the first and second chemical components intermix thereby causing formation of a visible mark at the occlusion contact points 25 (see FIG. 3).

Figure 2:
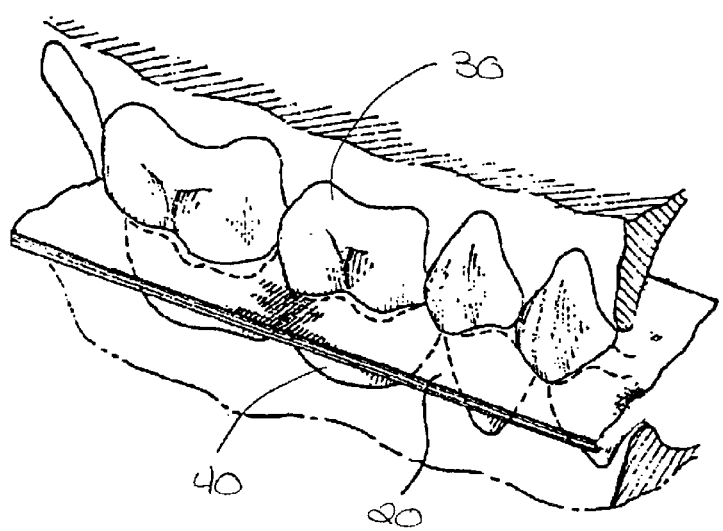
FIG. 2 is a perspective view showing an occlusion substrate inserted between occluded upper and lower arches of a patient or dental articulation device.
Figure 3:
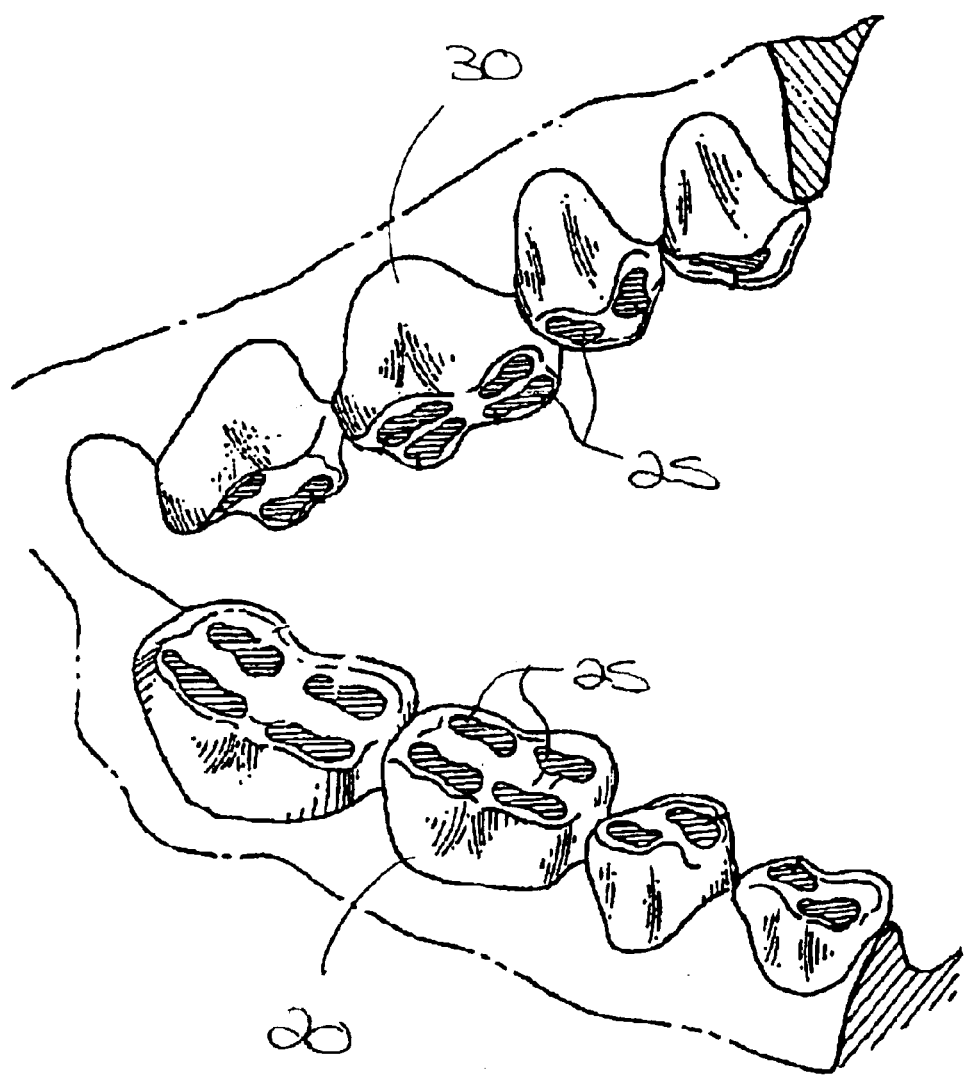
FIG. 3 is a perspective view showing exemplary formation of a visible mark at the occlusion contact points on the teeth of a patient or articulation device in accordance with one embodiment of the present invention.
Figure 4:
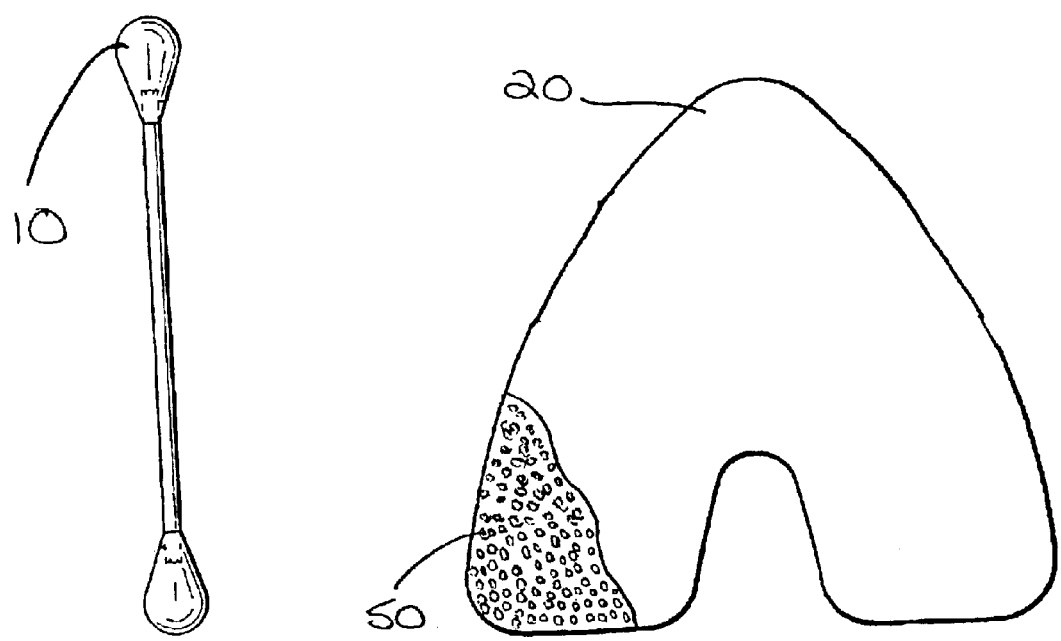
FIG. 4 is a plan view of an alternative embodiment of a dental articulation kit according to the invention.

The present invention further includes a method for performing a dental articulation test that is not limited to any particular articulation kit. According to one embodiment of the method of the present invention, the first chemical component is simply applied to at least one tooth of a patient or dental articulation device. A substrate sheet that contains a second chemical component of the binary marking system (e.g., the occlusion substrate 20) is inserted into the patient's mouth or articulation device such as shown in FIG. 2. The first and second arches of said patient or articulation device are then caused to occlude over said substrate, thereby causing formation of a visible mark at occlusion contact points 25 (see, e.g., FIG. 3).

While the embodiment of the invention illustrated in FIG. 1 utilizes an applicator substrate 10, which for example can consist of filter paper, to apply one of the components of the binary marking system to teeth, it will be appreciated that any suitable applicator device could be used in the kit and method of the present invention. For example, the applicator could consist of a brush, swab or spraying device. Advantageously, the applicator used to apply the first chemical to the teeth can include an absorbent material such as in the form of an absorbent substrate, pad or swab. When the kit or method of the present invention is used on the teeth of a patient, this absorbent material can be used to absorb at least some of the saliva present on and/or around the patient's teeth. The removal of the saliva helps to enhance the formation of the visible mark on the occlusion points thereby improving the test results.

To simplify performance of the test, one or both of the substrates 10, 20 can be sized or configured specifically for dental articulation tests. For example, in the illustrated embodiment, the occlusion substrate 20 has a generally horseshoe shaped configuration that conforms to the shape of a human dental arch. The configuration is not critical, but to the contrary any substitutes sized for human dental articulation may be employed. Any suitable substrate, such as paper, silk, foil, or the like may be employed in conjunction with the invention.

According to one embodiment of the invention, the binary marking system is pressure sensitive, by which is contemplated that the application of pressure beyond ordinarily ambient pressure is required to cause formation of a visible mark. In particular, a coating of pressure-rupturable microcapsules 50 containing the second chemical component of the binary marking system can be provided on at least one surface of the occlusion substrate 20 as shown in FIG. 1. These microcapsules 50 are designed to rupture and release the second chemical component when the teeth of a patient or articulation device occlude over the occlusion substrate 20. Once released from the microcapsules 50, the second chemical intermixes with the first chemical that was applied to the teeth. This results in a chemical reaction that produces the color formation or other visible mark formation. If a coating of microcapsules 50 is provided on both the upper and lower surfaces of the occlusion substrate 20, the occlusion substrate can be used to identify the occlusion contact points on both the upper and lower dental arches.

One example of a pressure sensitive binary marking system suitable for use in the present invention is the system used in carbonless paper. For instance, carbonless paper such as UltraMark CB 16.8 lb. white carbonless paper, which is available from Appleton Papers Inc. of Appleton, Wis., is one example of a substrate suitable for use as the occlusion substrate. Such sheets of carbonless paper include pressure-rupturable microcapsules containing a color forming material. A solvent can be used to facilitate contact of the first chemical compound with the second chemical compound of the binary marking system. Examples of solvents suitable for use in the microcapsules on the occlusion substrate include ethyldiphenylmethane (U.S. Pat. No. 3,996,405); benzylxylene (U.S. Pat. No. 4,130,299); alkyl biphenyls such as propylbiphenyl (U.S. Pat. No. 3,627,581) and butylbiphenyl (U.S. Pat. No. 4,287,074); dialkyl phthalates in which the alkyl groups thereof have from 4 to 13 carbon atoms, e.g. dibutyl phthalate, dioctylphthalate, dinonyl phthalate and ditridecylphthalate; 2,2,4-trimethyl-1, 3-pentanediol diisobutyrate (U.S. Pat. No. 4,027,065); $C_{10}$–$C_{14}$ alkyl benzenes such as dodecyl benzene; alkyl or aralkyl benzoates such as benzyl benzoate; alkylated naphthalenes such as dipropylnaphthalene (U.S. Pat. No. 3,806,463); partially hydrogenated terphenyls; high-boiling straight or branched chain hydrocarbons; and mixtures of the above. Vegetable oils, esters of vegetable oils and mixtures that include such vegetable oils can also be advantageous used. Vegetable oil based solvent systems for applications involving pressure-rupturable microcapsules are described in U.S. Pat. Nos. 5,177,051; 5,281,266; 5,464,803; 5,472,489; 5,476,829; 5,605,874 and 6,310,002.

A chromogenic material preferably is included in the microcapsules on the occlusion substrate along with any of the above solvents. The solvent in the microcapsules facilitates the transfer of the chromogenic material to the acidic developer material which is the other component of the binary marking system.

The chromogen or chromogenic materials are electron donating dye precursors also known as colorformers. The chromogenic materials are typically colorless or lightly colored in one state, and express an observable color when contacted with an acidic developer material. These colorformers include phthalide, leucauramine and fluoran compounds. Chromogenic materials also include Crystal Violet Lactone (3,3-bis(4-dimethylaminophenyl)-6-dimethylaminophthalide, U.S. Pat. No. RE. 23,024); phenyl-, indol-, pyrrol- and carbazol-substituted phthalides (for example, in U.S. Pat. Nos. 3,491,111; 3,491,112; 3,491,116; 3,509,174); nitro-, amino-, amido-, sulfonamido-, aminobenzylidene-, halo-, anilino-substituted fluorans (for example, in U.S. Pat. Nos. 3,624,107; 3,627,787; 3,641,011; 3,642,828; 3,681,390); spiro-dipyrans (U.S. Pat. No. 3,971,808); and pyridine and pyrazine compounds (for example, in U.S. Pat. Nos. 3,775,424 and 3,853,869). Other eligible chromogenic materials include: 3-diethylamino-6-methyl-7-anilino-fluoran (U.S. Pat. No. 3,681,390); 2-anilino-3-methyl-6-dibutylamino-fluoran (U.S. Pat. No. 4,510,513) also known as 3-dibutylamino-6-methyl-7-anilino-fluoran; 3-dibutylamino-7-(2-chloroanilino)fluoran; 3-(N-ethyl-N-tetrahydrofurfurylamino)-6-methyl-7-3-5'6-tris(diniethylamino)spiro[9H-fluorene-9'1 (3'H)-isobenzofuran]-3'-one; 7-(1-ethyl-2-methylindol-3-yl)-7-(4-diethylamino-2-ethoxyphenyl)-5,7-dihydrofuro[3,4-b]pyridin-5-one (U.S. Pat. No. 4,246,318); 3-diethylamino-7-(2-chloroanilino) fluoran (U.S. Pat. No. 3,920,510); 3-(N-methylcyclohexylamino)-6-methyl-7-anilino-fluoran (U.S. Pat. No. 3,959,571); 7-(1-octyl-2-methylindol-3-yl)-7-4-(4-diethylamino-2-ethoxy-phenyl)-5,7-dihydrofuro [3,4-b] pyridin-5-one; 3-diethylamino-7,8-benzofluoran; 3,3-bis(1-ethyl-2-methylindol-3-yl) phthalide; 3-diethylamino-7-anilino-fluoran; 3-diethylamino-7-benzylamino-fluoran; 3'-phenyl-7-dibenzylamino-2,2'-spiro-di-[2H-1-benzopyran]; 6' [ethyl(3-methylbutyl)amino]-3'-methyl-2' (phenylamino)-spiro[isobenzofuran-1(3H), 9'-[9H] xanthen]-3-one; 6 -(dimethylamino-3,3-bis(4-(dimethylamino)phenyl)-1(3H)-isobenzofuranone (crystal violet lactone); 3-diethylamino-6-methyl-7-(2,4-dimethylphenyl)aminofluoran and mixtures of any of the foregoing. The or crystalline forms, of some of the fluourans, where such are known, are equally functional.

Opposite positioning of the binary components from the configuration normally employed in connection with carbonless paper can also be useful. Such variation in this application can involve microencapsulating the solvent and acidic developer and coating onto the occlusion substrate. If the acidic developer is selected to be liquid, the developer can perform the function of the solvent as well. The chromogenic material in such variation can be applied in its colorless form to the teeth of the patient, or to the absorbent material for application to the patient's teeth. The occlusion substrate is then relied upon to transfer the developer material to colorize the chromogen when pressure is applied sufficient to rupture the microcapsules. For instance, the occlusion substrate can be coated with developer material. A common example of such arrangement is carbonless CF paper.

The chromogen could be applied as a solution directly to the teeth of the patient or via the absorbent material. It is possible, though not preferred, to forego the capsules altogether in such a variation. The use of microencapsulated chromogen is believed to provide a higher level of definition of the dental occlusion contact points. A liquid solution that eliminates the occlusion substrate could involve forming a slurry or paste or other thixotropic mixture of chromogen suspended in a waxy or semi-liquid developer material. The binary marking system can be formed as such a coating paste or thixotropic solution. Such a composition can be prepared which includes a fine dispersion of the chromogenic material, encapsulated or unencapsulated in a base of acidic clay with optional other fillers, waxes or binders to form a paste. A common example of such compositions is the slurries used in forming thermally imaged papers or carbonless self-contained dispersions. The materials would be selected to cause formation of a visible mark at ambient temperatures with the frictional contact of the teeth sufficient to enable the formation of a visible mark when the capsules are ruptured or pressure applied to the paste to facilitate intimate reactive contact between developer and chromogenic material. Optionally, chromogenic material can be encapsulated together with solvent and formed into a slurry suspension in a liquid or semiliquid developer material. It is also possible to form two populations of microcapsules, with the first population encapsulating chromogenic material and the second population encapsulating developer. A slurry mixture of such capsules could be directly coated to the surface of the teeth. The microcapsules thus applied to the teeth can optionally contain solvent and chromogenic material. The occlusion substrate in such variation contains a coating of a developer material such as an acidic clay or resin. More generally, any configuration whereby a visible effect is formed, preferably only upon the application of pressure, may be employed in conjunction with the invention.

The microcapsules can be prepared by processes well known in the art such as from gelatin as disclosed in U.S. Pat. Nos. 2,800,457 and 3,041,289; or, more preferably, from urea-formaldehyde resin and/or melamine-formaldehyde resin as disclosed in U.S. Pat. Nos. 4,001,140; 4,081,376; 4,089,802, 4,100,103; 4,105,823; 4,444,699 or 4,552,811.

When using such carbonless paper as the occlusion substrate, the first chemical of the binary marking system which is applied using the applicator substrate can consist of any material that combines with the material used in the microcapsules. While the amounts used should be small, if the first chemical component is going to be applied to the teeth of a patient as opposed to a dental articulation device, it may be desirable to use an aqueous solution of dentally compatible organic acid such as pectin or another Lewis acid.

Other chemicals that could be used include clays; treated clays (U.S. Pat. Nos. 3,622,364 and 3,753,761); aromatic carboxylic acids such as salicylic acid; derivatives of aromatic carboxylic acids and metal salts thereof (U.S. Pat. No. 4,022,936); phenolic developers (U.S. Pat. No. 3,244,550); acidic polymeric material such as phenol-formaldehyde polymers, etc. (U.S. Pat. Nos. 3,455,721 and 3,672,935); and metal-modified phenolic resins (U.S. Pat. Nos. 3,732,120; 3,737,410; 4,165,102; 4,165,103; 4,166,644 and 4,188,456). Additional details regarding the pressure sensitive binary marking systems used in carbonless paper are provided in U.S. Pat. Nos. 2,730,456; 3,565,666; 3,955,026 and 4,596, 996. The disclosures of all of the mentioned patents are incorporated herein by reference. The chemistries employed in some patents are not contemplated as exclusive, but to the contrary any binary marking system that includes first and second reactants that combine to form a visible indicia may be used in conjunction with the invention.

While an exemplary embodiment of the present invention has been described in relation to a binary marking system such as is used in carbonless paper, it will be understood that the present invention is not limited to such a binary marking system. For example, the chemical component provided on the occlusion substrate does not have to be microencapsulated. Moreover, the placement of the two chemical components could be reversed with the microencapsulated component being applied to the teeth. Thus it will be appreciated that any suitable binary marking system consisting of first and second components that produce a visible effect when they are intermixed can be used.

In accordance with an alternative embodiment of the present invention, the dental articulation test method and related kit can be modified such that light is emitted from one or more teeth at the occlusion contact points. This embodiment utilizes a binary system comprising first and second chemical components that produce a light emitting or luminous effect when intermixed. The light-emitting property may be visible in the absence of electromagnetic radiation or upon exposure to electro magnetic radiation (e.g. "black" light). Specifically, a first chemical component of the binary luminous marking system may be applied to the teeth of a patient or articulation device using any suitable applicator such as, for example, a substrate, swab, or spray. In turn, the occlusion substrate carries the second component of the binary system. This component on the occlusion substrate may or may not be microencapsulated. One example of a suitable chemical component for use on the occlusion substrate is fluorecene, although other chemicals could also be used. When the teeth of the patient or dental articulation device occlude over the substrate, luminous markings adhere to the teeth at the occlusion contact points. A black light may be used to assist in viewing the luminous markings on the teeth.

Alternatively, the occlusion substrate can simply include a coating of a light emitting or luminous material. Again, the material may be light emitting in the absence of electromagnetic radiation or upon exposure to electromagnetic radiation. Preferably, but not necessarily, the light-emitting material is microencapsulated. When the teeth of the patient or dental articulation device occlude over the substrate, the microcapsules rupture and release the light emitting material, which then adheres to the teeth at the occlusion contact points. The luminous material also may be coated onto the occlusion substrate without the use of microcapsules. Additionally, a second chemical component may be applied to the teeth to assist in the transfer of the light emitting or luminous material to the teeth. In accordance with another embodiment, the light-emitting material may be applied directly to a tooth of a patient or articulation device, with or without the use of a substrate. First and second arches of the patient or device are caused to occlude, where upon a mark is formed at occlusion contact points. The light-emitting material may be provided on a suitable substrate or without a substrate (e.g. by swabbing or spraying onto the tooth). If used, the substrate may be a thin substrate (such as a paper or film) having light-emitting material disposed on one or both sides thereof.

It is thus seen that the invention provides methods and kits useful in conjunction with dental articulation.

All references cited herein are hereby incorporated by reference.

All methods described herein can be performed in any suitable order unless otherwise indicated herein or otherwise clearly contradicted by context. The use of any and all examples, or exemplary language provided herein does not pose a limitation on the scope of the invention unless otherwise claimed. No language in the specification should be construed as indicating any non-claimed element as essential to the practice of the invention. The terms "first and second" when describing components in the claims should be construed only with reference to the claim in which such terms are used, or in a prior claim from which such claim depends, and it is not necessarily intended for these terms to be used consistently from one group of claims to another.

Preferred embodiments of this invention are described herein, including the best mode known to the inventors for carrying out the invention. Variations of those preferred embodiments may become apparent to those of ordinary skill in the art upon reading the foregoing description. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for dental articulation, comprising in any appropriate order applying to a tooth of a patient an absorbent material that includes a first chemical component of a binary marking system;

allowing at least a portion of said first binary chemical component to deposit on to said tooth and at least a portion of the patient's saliva to become absorbed by said absorbent material;

inserting into the patient's mouth a substrate that includes a second chemical component of said binary marking system;

causing the patient's teeth to occlude over said substrate thereby causing formation of a visible mark at occlusion contact points.

2. A method according to claim 1, said substrate comprises a sheet having a first side and a second side, said second chemical component being provided as a coating of microencapsulated chemical component disposed on at least one of said first side and said second side of said sheet.

3. A method according to claim 2, said sheet having a coating of microcapsules containing said second chemical component on said first side and said second side of said sheet.

4. A dental articulation kit comprising:

an absorbent substrate, said substrate comprising an absorbent material and including a first chemical component of a binary marking system;

a second substrate including a second chemical component of binary marking system, said first and second substrates being sized for human dental articulation.

5. A dental articulation kit according to claim 4, said second substrate comprising a sheet having first and second sides, said second chemical component being present as a coating of miroencapsulated second chemical component disposed on at least said first side of said sheet.

6. A dental articulation kit according to claim 5, said sheet having a coating of microcapsules containing said second chemical component disposed on each of said first side and said second side of said sheet.

7. A method for dental articulation, comprising;
applying to at least one tooth of a patient or articulation device a first chemical component of a binary marking system;
inserting into the patient's mouth or articulation device a substrate sheet that contains a coating of microcapsules disposed on at least one side thereof, at least some of said microcapsules containing a second chemical component of said binary marking system;
causing first and second arches of said patient or articulation device to occlude over said substrate, thereby causing formation of a visible mark at occlusion contact points.

8. A method according to claim 7, said tooth being the tooth of a patient.

9. A method according to claim 8, said tooth being the tooth of a dental articulation device.

10. A method according to claim 9, said substrate sheet having a coating of microcapsules disposed on each side of said sheet, at least some of said microcapsules containing said second chemical component.

11. A method according to claim 10, said first chemical component comprising a dentally compatible Lewis acid.

12. A method according to claim 11, said first chemical component comprising pectin.

13. A method for dental articulation, comprising;
applying to at least one tooth of a patient or articulation device a substrate sheet that includes a coating of microcapsules disposed on at least one side thereof;
causing first and second arches of said patient or articulation device to occlude over said substrate whereby at least some of said microcapsules rupture thereby releasing a material contained in said microcapsule at occlusion contact points, said material comprising a material that causes light to be emitted from said tooth at said occlusion contact points.

14. A method according to claim 13, said tooth being the tooth of a patient.

15. A method according to claim 13, said tooth being the tooth of a dental articulation device.

16. A method according to claim 13, said substrate sheet having a coating of microcapsules disposed on each side of said sheet, at least some of said microcapsules containing said material.

17. A method according to claim 13, said material comprising fluorecene.

18. A dental articulation kit comprising:
at least one substrate have first and second sides and include a coating of a microencapsulated first binary chemical component of a binary marking system disposed on at least one of said first and second sides;
a quantity of a second binary chemical component of said binary marking system sufficient to apply to at least one tooth of a patient or articulation device to enable dental articulation; and
an applicator for said second binary chemical component.

19. A dental articulation kit according to claim 18, said substrate having a coating of microencapsulated first binary chemical components on said first side and said second side of said substrate.

20. A dental articulation kit according to claim 18, said second binary component comprising a dentally compatible Lewis acid.

21. A dental articulation kit according to claim 18, said second binary component comprising pectin.

22. A dental articulation kit according to claim 18, the applicator comprising a swab.

23. A dental articulation kit according to claim 18, the applicator comprising an absorbent material.

24. A dental articulation kit according to claim 18, said substrate being shaped to generally conform to a human dental arch.

25. A method for dental articulation, comprising:
applying to at least one tooth of a patient or articulation device a first chemical component of a binary marking system including first and second chemical components which produce a luminous effect when intermixed;
inserting into the patient's mouth or articulation device a substrate that includes the second chemical component of said binary marking system;
causing first and second arches of said patient or articulation device to occlude over said substrate, thereby creating a luminous mark on said tooth at occlusion contact points.

26. A method according to claim 25, said tooth being the tooth of a patient.

27. A method according to claim 25, said tooth being the tooth of a dental articulation device.

28. A method according to claim 25, said substrate sheet having a coating of microcapsules disposed on each side of said sheet, at least some of said microcapsules containing said second chemical component.

29. A method for dental articulation, comprising;
applying to at least one tooth of a patient or articulation device a mixture of a first chemical component and a second chemical component of a binary marking system, said first and second chemical components being separate in said mixture but reactive to form a visible mark upon application of pressure;
causing first and second arches of said patient or articulation device to occlude, thereby causing formation of said visible mark at occlusion contact points.

30. A method according to claim 29, said tooth being the tooth of a patient.

31. A method according to claim 29, said tooth being the tooth of a dental articulation device.

32. A method according to claim 29, said first chemical component comprising a dentally compatible Lewis acid.

33. A method according to claim 29, said second chemical component comprising or being contained in a liquid, said mixture comprising a dispersion of microcapsules in said liquid, said microcapsules containing said first chemical component.

34. A method according to claim 29, said mixture being a thixotropic mixture.

35. A method according to claim 29, at least one of said first and second chemical components being microencapsulated.

36. A method according to claim 29, said first and second chemical components each being microencapsulated.

37. A method according to claim 29, said first chemical component comprising pectin.

38. A dental articulation kit comprising:
a mixture of a first chemical component and a second chemical component of a binary marking system, said first and second chemical components being separate in said mixture but reactive to form a visible mark upon application of pressure; and an applicator for said mixture.

39. A dental articulation kit according to claim 38, comprising a pair of applicators for said mixture.

40. A dental articulation kit according to claim 38, said first chemical component comprising a dentally compatible Lewis acid.

41. A dental articulation kit according to claim 38, said first chemical component comprising pectin.

42. A dental articulation kit according to claim 38, the applicator comprising a swab.

43. A dental articulation kit according to claim 38, the applicator comprising an absorbent material.

44. A method for dental articulation, comprising;

applying to at least a first tooth of a first arch of a patient or articulation device a first material;

applying to at least a second tooth of a second arch of said patient or articulation device a second material, said first and second chemical materials being reactive to form a visible mark upon application of pressure;

causing first and second arches of said patient or articulation device to occlude, thereby causing formation of a visible mark at occlusion contact points.

45. A method according to claim 44, said first and second teeth being those of a patient.

46. A method according to claim 44, said first and second teeth being those of a dental articulation device.

47. A method according to claim 44, said first chemical component comprising a dentally compatible Lewis acid.

48. A method according to claim 44, said first chemical component comprising pectin.

49. A method according to claim 44, at least one of said first and second chemical components being microencapsulated.

50. A method according to claim 44, said first and second chemical components each being microencapsulated.

51. A dental articulation kit comprising:

a first container containing a first material and a second container containing a second material, said first and second materials being reactive to form a visible mark upon application of pressure; and an applicator for said first and second materials.

52. A dental articulation kit according to claim 51, comprising a pair of applicators for said first and second materials.

53. A dental articulation kit according to claim 51, said first material comprising a dentally compatible Lewis acid.

54. A dental articulation kit according to claim 52, said first material comprising pectin.

55. A dental articulation kit according to claim 51, the applicator comprising a swab.

56. A dental articulation kit according to claim 38, the applicator comprising an absorbent material.

57. A device comprising:

a substrate, said substrate being sized for dental articulation; and a light-emitting material coated on said substrate, said light-emitting material being transferable to the tooth of a patient or articulation device upon the application of pressure.

58. A device according to claim 57, said substrate comprising a thin substrate having a first side and a second side, said light-emitting material being coated on said first side and said second side.

59. A device according to claim 57, said light-emitting material emitting light in the absence of exposure to electromagnetic radiation.

60. A device according to claim 57, said light-emitting material emitting light upon exposure to electromagnetic radiation.

61. A method for dental articulation, comprising:

applying to the tooth of a patient or articulation device a light-emitting material; and causing first and second arches of said patient or articulation device to occlude, thereby causing formation of a mark at occlusion contact points.

62. A method according to claim 61, said light-emitting material emitting light in the absence of exposure to electromagnetic radiation.

63. A method according to claim 61, said light-emitting material emitting light upon exposure to electromagnetic radiation.

64. A method according to claim 61, said method comprising introducing a substrate containing said light-emitting material to the tooth of said patient or articulation device.

65. A method according to claim 61, said method including applying said light-emitting material in liquid form to said tooth.

66. A method according to claim 65, said light-emitting material being sprayed onto said tooth.

* * * * *